(12) United States Patent
Dunn et al.

(10) Patent No.: US 10,524,917 B2
(45) Date of Patent: Jan. 7, 2020

(54) IMPLANT SURFACES

(71) Applicant: Ossis Limited, Christchurch (NZ)

(72) Inventors: Timothy John Dunn, Christchurch (NZ); Peter James Burn, Christchurch (NZ); Nicholas McKenzie Smyth, Christchurch (NZ)

(73) Assignee: Ossis Limited, Christchurch (NZ)

( * ) Notice: Subject to any disclaimer, the term of this patent is extended or adjusted under 35 U.S.C. 154(b) by 0 days.

(21) Appl. No.: 15/316,461

(22) PCT Filed: May 14, 2015

(86) PCT No.: PCT/NZ2015/050057
§ 371 (c)(1),
(2) Date: Dec. 5, 2016

(87) PCT Pub. No.: WO2015/187038
PCT Pub. Date: Dec. 10, 2015

(65) Prior Publication Data
US 2017/0143495 A1    May 25, 2017

(30) Foreign Application Priority Data
Jun. 5, 2014 (NZ) ........................ 625956

(51) Int. Cl.
*A61F 2/34*    (2006.01)
*A61F 2/30*    (2006.01)

(52) U.S. Cl.
CPC ............ *A61F 2/34* (2013.01); *A61F 2/30771* (2013.01); *A61F 2/30907* (2013.01);
(Continued)

(58) Field of Classification Search
CPC ..... A61B 17/1746; A61B 17/15; A61B 17/17; A61B 2017/568; A61F 2/34
See application file for complete search history.

(56) References Cited

U.S. PATENT DOCUMENTS

| 4,437,193 A | 3/1984 | Oh |
| 4,904,265 A | 2/1990 | MacCollum et al. |

(Continued)

FOREIGN PATENT DOCUMENTS

WO    2011156504 A3    12/2011

OTHER PUBLICATIONS

International Search Report for International Application No. PCT/NZ2015/050057, dated Sep. 1, 2015, Applicant, TI Holdings Limited (9 pages).

(Continued)

*Primary Examiner* — Alvin J Stewart
(74) *Attorney, Agent, or Firm* — Richards Patent Law P.C.

(57) ABSTRACT

The implants of the invention relate to improved implants formed using additive manufacturing techniques, the implants including a hemispherical cup portion, and an ischium flange, a pubic ramus flange and an ilium flange, each flange extending outwardly from the perimeter of the hemispherical cup portion, wherein the implant surface includes an area of integrally formed three dimensional scaffold on the bone apposition surfaces of the cup portion and on a bone apposition surface of at least one of the flanges of the implant. The invention also relates to implants with different surface texture and alignment features, together with methods for the manufacture of patient-specific implants of the invention.

17 Claims, 8 Drawing Sheets

(52) U.S. Cl.
CPC ...... *A61F 2/30942* (2013.01); *A61F 2/30744* (2013.01); *A61F 2002/30578* (2013.01); *A61F 2002/30617* (2013.01); *A61F 2002/30688* (2013.01); *A61F 2002/30774* (2013.01); *A61F 2002/30787* (2013.01); *A61F 2002/30838* (2013.01); *A61F 2002/30914* (2013.01); *A61F 2002/30962* (2013.01); *A61F 2002/3401* (2013.01); *A61F 2002/3403* (2013.01); *A61F 2002/3404* (2013.01); *A61F 2002/3429* (2013.01); *A61F 2002/3483* (2013.01)

(56) References Cited

U.S. PATENT DOCUMENTS

| | | | |
|---|---|---|---|
| 5,141,680 A * | 8/1992 | Almquist | B29C 41/12 |
| | | | 118/120 |
| 6,944,518 B2 * | 9/2005 | Roose | A61F 2/30942 |
| | | | 623/22.21 |
| 6,993,406 B1 | 1/2006 | Cesarano et al. | |
| 9,498,234 B2 * | 11/2016 | Goldstein | A61B 17/15 |
| 2003/0171818 A1 | 9/2003 | Lewallen | |
| 2005/0021148 A1 | 1/2005 | Gibbs | |
| 2005/0065628 A1 * | 3/2005 | Roose | A61F 2/30942 |
| | | | 700/117 |
| 2005/0148843 A1 * | 7/2005 | Roose | A61B 17/17 |
| | | | 600/407 |
| 2011/0029092 A1 | 2/2011 | Deruntz et al. | |
| 2011/0272276 A1 | 11/2011 | Thull et al. | |
| 2012/0289965 A1 * | 11/2012 | Gelaude | A61B 17/15 |
| | | | 606/87 |
| 2013/0035766 A1 | 2/2013 | Miridrew | |
| 2014/0052270 A1 | 2/2014 | Witt et al. | |
| 2014/0135940 A1 * | 5/2014 | Goldstein | A61B 17/15 |
| | | | 623/22.21 |
| 2015/0134063 A1 * | 5/2015 | Steinmann | A61F 2/30907 |
| | | | 623/17.16 |
| 2015/0258735 A1 * | 9/2015 | O'Neill | A61F 2/30771 |
| | | | 264/497 |
| 2016/0287395 A1 * | 10/2016 | Khalili | A61F 2/30942 |
| 2016/0296289 A1 * | 10/2016 | Choudhury | A61F 2/30942 |

OTHER PUBLICATIONS

Written Opinion for International Application No. PCT/NZ2015/050057, dated Sep. 1, 2015, Applicant, TI Holdings Limited (8 pages).

* cited by examiner

IMPLANT SURFACES

CROSS-REFERENCE TO RELATED APPLICATIONS

This application is a U.S. National Stage Entry of PCT/NZ2015/050057 filed May 14, 2015, which claims the benefit of priority to New Zealand Patent Application No. 625956 filed Jun. 5, 2014, both of which are incorporated in their entireties by reference.

TECHNICAL FIELD

This invention relates to improved bone replacement implants, methods for their use and the manufacture thereof.

BACKGROUND ART

Successful placement and attachment of an orthopaedic implant to patient bone is essential in securing successful patient outcomes for people undergoing bone replacement surgery.

Some of the disadvantages and problems with current techniques are discussed below with reference to the acetabular region, however such issues are common across all regions where bone replacements are conducted, including the knee, elbow, shoulder to name a few.

Typical acetabular augmentation occurs during the process of total hip replacement. During the augmentation process, an acetabular implant is placed within the patient's acetabulum and is designed to engage the head of a replacement femoral implant or femoral implant.

Failure or sub-optimal incorporation of the replacement implant is common and may be associated with one or more design features of implants currently used for an acetabular or other bone replacement. Such features include the polished surfaces present in common bone implants that make osseointegration difficult, sub-optimal levels of surface scaffolding associated with the implant, difficulty in positioning and alignment of the implant, or structural disadvantages that result in the inability of the surgeon to effectively place, secure and pack bone graft behind the implant.

It is the object of the present invention to address one or more of these issues to improve success rates of bone replacement surgeries through improved implant design, manufacturing methods and/or methods for implant use, or at least to overcome some of the disadvantages.

Alternatively, it is the object of the present invention to at least provide the public with a useful choice.

It is an object of the present invention to address the foregoing problems or at least to provide the public with a useful choice.

All references, including any patents or patent applications, cited in this specification are hereby incorporated by reference. No admission is made that any reference constitutes prior art. The discussion of the reference states what their authors assert, and the applicants reserve the right to challenge the accuracy and pertinency of the cited documents. It will be clearly understood that, although a number of prior art publications are referred to herein, this reference does not constitute an admission that any of these documents forms parts of the common general knowledge in the art, in New Zealand or in any other country.

Further aspects and advantages of the present invention will become apparent from the ensuing description which is given by way of example only.

SUMMARY OF THE INVENTION

Preferred aspects of the invention are set forth in the appended claims. Particular embodiments are described below in non-limiting terms.

According to a first embodiment of the invention there is provided an orthopaedic implant, wherein the implant surface includes an area of integrally formed three dimensional scaffold on two or more bone apposition surfaces associated with the implant.

In preferred embodiments of the invention, the implant includes three dimensional scaffold on every bone apposition surface within the implant.

In preferred embodiments, the implant includes one or more flanges and the three dimensional scaffold is located on one or more implant flange surfaces and/or flange edges and/or over flange corners.

In further preferred embodiments, the implant includes a hemispherical cup portion, wherein the outer convex surface of the cup portion includes three dimensional scaffold.

Preferably, the implant is a patient-specific implant.

Preferably, the implant is a femoral implant or an acetabular implant.

More preferably, the implant is a tri-flange acetabular implant including an ischial flange, a pubic ramus flange and an ilium flange.

Preferably the ischium flange, ilium flange and/or pubic ramus flange include three dimensional scaffold across substantially all their surfaces.

Alternatively, the ischium flange, ilium flange and/or pubic ramus flange include three dimensional scaffold on the surface adapted to connect to patient bone.

In further preferred embodiments of the invention there is provided an orthopaedic implant, wherein the three dimensional scaffold and implant are integrally formed.

More preferably, the implant and three dimensional scaffold are integrally formed using additive manufacturing technology.

In alternative embodiments, the three dimensional scaffold is applied to the implant following implant manufacture.

In further preferred embodiments, the three dimensional scaffold is formed using a modified dodecahedron structure.

In alternative embodiments, the three dimensional scaffold is formed using a trabecular mesh structure.

In further embodiments the implant includes an open mesh three dimensional scaffold on selected surface areas on the implant for the ingrowth of soft and hard tissues, wherein the open mesh scaffold has a unit cell size of between 1.0 mm and 3.0 mm, and a 200-1,000 micron element.

More preferably, the three dimensional scaffold has a unit cell size of between 1.2 mm-2.0 mm.

Preferably, the three dimensional scaffold has a porosity of between 50% and 80%.

In further preferred embodiments of the invention the area of three dimensional scaffold further includes an antibacterial coating. This coating may be applied following manufacture of the implant, or included within the material used for integrally forming the implant during additive manufacturing.

More preferably, the antibacterial coating is an antibacterial coating including silver.

In more preferred embodiments, the implant includes one or more suture holes.

More preferably, the implant is an acetabular implant and includes one or more suture holes located on the hemispherical cup of the implant.

More preferably, the implant includes between one and ten suture holes.

More preferably, the suture holes are circular or elliptical in shape.

Preferably, the one or more suture holes are located 5-40 mm from the edge of the hemispherical cup.

According to a second embodiment of the invention there is provided a method for the manufacture of a patient-specific orthopaedic implant wherein the implant surface includes an area of integrally formed three dimensional scaffold on two or more bone apposition surfaces associated with the implant, the method including the steps of;
 a) extracting patient-specific information regarding a patient's specific bone geometry at an augmentation site;
 b) designing a patient-specific implant based on said information, the implant including one or more regions of three dimensional scaffold located on one or more bone apposition surfaces;
 c) manufacturing implant based on design of step (b) using additive manufacturing techniques and wherein the manufacturing includes the step of integrally forming the three dimensional scaffold with the implant.

Preferably, the method includes the step of integrally forming three dimensional scaffold on every bone apposition surface within the implant.

Preferably the method includes the step of forming an implant with one or more flanges, the three dimensional scaffold integrally formed on one or more implant flange surface and/or flange edges.

Preferably the method includes the step of integrally forming an implant including a cup portion, wherein the convex outer surface of the cup portion includes three dimensional scaffold.

Preferably, the method includes manufacturing a femoral implant or an acetabular implant.

More preferably, the method includes manufacturing a tri-flange acetabular implant including an ischium flange, a pubic ramus flange and an ilium flange.

Preferably the method includes the steps of including three dimensional scaffold substantially across every surface of the ischium flange, ilium flange and/or pubic ramus flange.

Alternatively the method includes including three dimensional scaffold on the surfaces adapted to connect to patient bone.

In further preferred embodiments, the method includes the step of forming three dimensional scaffold using a substantially dodecahedron structure.

In alternative embodiments, the method includes the step of forming three dimensional scaffold using a substantially trabecular mesh structure.

In further preferred embodiments, the method further includes the step of forming one or more suture holes in the implant.

More preferably, when the method includes manufacturing an acetabular implant, the method includes the step of forming one or more suture holes on the hemispherical cup of the implant.

In further preferred methods, the method includes the further step of application of an antibacterial coating, preferably an ion beam silver sputter coating.

Preferably, the additive manufacturing method is electron beam melting (EBM) manufacturing.

According to a third embodiment of the invention there is provided a bone replacement implant, wherein the implant surface includes at least one area of three dimensional scaffold and at least one area of roughened, textured surface.

Preferably, the roughened surface texture is located on substantially all outwardly facing surfaces of the implant not covered with three dimensional scaffold.

In further preferred embodiments, the bone replacement implant is an acetabular implant.

More preferably, the acetabular implant includes roughened surface texture on substantially all outwardly facing surfaces of the implant not covered with three dimensional scaffold with the exception of the medial wall of the acetabular rim of the implant.

More preferably, a portion of the medial wall of the acetabular rim is a polished surface to allow sliding of tendons across the implant once positioned.

Preferably the implant surface including an area of roughened, textured surface has a surface roughness Ra value of between substantially 1 and 25 µm.

In further preferred embodiments of the invention the area of roughened surface texture further includes an antibacterial coating. This coating may be applied following manufacture of the implant, or included within the material used for integrally forming the implant during additive manufacturing.

More preferably, the antibacterial coating is an antibacterial coating including silver.

In more preferred embodiments, the implant includes one or more suture holes.

More preferably, the implant is an acetabular implant and includes one or more suture holes located on the hemispherical cup of the implant.

More preferably, the implant includes between one and ten suture holes.

More preferably, the suture holes are circular or elliptical in shape.

Preferably, the one or more suture holes are located 5-40 mm from the edge of the hemispherical cup.

According to a fourth embodiment of the invention there is provided a method for the manufacture of a patient-specific bone replacement implant wherein the implant surface includes at least one area of three dimensional scaffold and at least one area of roughened, textured surface the method including the steps of;
 a) extracting patient-specific information regarding a patient's specific bone geometry at said implantation site;
 b) designing a patient-specific implant based on said information, the implant including one or more regions of three dimensional scaffold and at least one area of roughened, textured surface;
 c) manufacturing implant based on design of step (b) using additive manufacturing techniques and wherein the manufacturing includes the step of integrally forming the three dimensional scaffold and textured surface with the implant;
 d) blasting the textured surface and polishing any untextured surface.

Preferably, the method includes the step of integrally forming a roughened, textured surface on all outwardly facing external surfaces of the implant not covered with three dimensional scaffold.

In further preferred embodiments, the bone replacement implant formed by the method is an acetabular implant.

More preferably, the method includes the step of forming roughened surface texture on substantially all outwardly facing surfaces of the implant not covered with three dimensional scaffold with the exception of the medial wall of the acetabular rim.

More preferably, the method includes the further step of polishing a portion of the medial wall of the medial acetabular rim to produce a substantially smooth finish.

Preferably the implant surface including an area of roughened, textured surface has a surface roughness Ra value of between substantially 1 and 25 µm.

Preferably the area of smooth finish has a surface Ra value of less than 1.

In further preferred embodiments, the method further includes the step of forming one or more suture holes in the implant.

More preferably, when the method includes manufacturing an acetabular implant, the method includes the step of forming one of more suture holes on the ilium flange of the implant.

In further preferred methods, the method includes the further step of application of an antibacterial coating, preferably an ion beam silver sputter coating.

Preferably, the additive manufacturing method is electron beam melting (EBM) manufacturing.

According to a fifth embodiment of the invention there is provided a patient-specific bone replacement implant, wherein the implant includes at least one integrally formed guide means for facilitating correct alignment of the implant within a patient.

In preferred embodiments of the invention the implant includes one or more integrally formed guide means adapted to enable correct rotational positioning and one or more guide means adapted to enable correct linear positioning with respect to a recipient patient's bone geometry.

Preferably, the guide means is a raised or depressed feature on the implant surface. In preferred embodiments of the invention the patient-specific bone replacement implant is an acetabular implant.

More preferably, the implant is a tri-flange acetabular implant including a hemispherical acetabular cup, an ilium flange, an ischium flange and a pubic ramus flange.

Preferably, the acetabular implant includes a linear orientation marker on the ischium flange and/or pubic ramus flange of the implant.

Even more preferably, the orientation marker is in the form of a line and is positioned on the implant so as to lie substantially parallel with the patient's pubic ramus ridge when the implant is inserted in a correct position within a patient.

In further preferred aspects of the invention the implant includes a guide means in the form of a projection adapted to engage with patient bone when the implant is correctly seated within the patient.

More preferably, the projection is adapted to engage with a patient's acetabular notch when the implant is correctly seated within the patient.

Preferably, the projection is an elongate projection extending outwardly from an upper region of the acetabular cup between the ischium flange and pubic ramus flange of the implant.

More preferably, the projection is an elongate projection extending outwardly from an upper region of the acetabular cup between the ischium flange and pubic ramus flange, wherein the projection extends at an angle of at least 60° from the external wall of the acetabular cup.

More preferably, the projection extends at an angle of at least 90° from the external wall of the acetabular cup.

More preferably, the projection includes a bend or curve.

Preferably, the projection includes a bend or curve of at least substantially 60° or more along the length of the projection, the bend or curve angling the projection downwards towards the base of the acetabular cup.

More preferably, the projection includes a bend or curve of substantially 90° or more. In further embodiments the projection surface includes an area of three dimensional scaffold or roughened surface area.

More preferably, the three dimensional scaffold is integrally formed with the projection surface.

In more preferred embodiments, the implant includes one or more suture holes.

More preferably, the implant is an acetabular implant and includes one or more suture holes located on the hemispherical cup of the implant.

More preferably, the implant includes between one and ten suture holes.

More preferably, the suture holes are circular or elliptical in shape.

Preferably, the one or more suture holes are located 5-40 mm from the edge of the hemispherical cup.

According to a sixth embodiment of the invention there is provided a method for the manufacture of a patient-specific bone replacement implant including at least one integrally formed guide means for facilitating correct alignment of the implant within a patient, the method including the steps of;
  a) extracting patient-specific information regarding a patient's specific bone geometry at a specific implantation site;
  b) designing a patient-specific implant based on said information, the implant including one or more guide means for facilitating correct alignment of the implant within a patient;
  c) manufacturing implant based on design of step (b) using additive manufacturing techniques.

In preferred embodiments of the invention the method of steps b) and c) includes forming a guide means in the form of a directional indicator.

Preferably, the implant is an acetabular implant.

More preferably, the implant is a tri-flange acetabular implant including an ilium flange, ischium flange and pubic ramus flange.

In preferred embodiments of the invention the guide means of steps b) and c) is a linear orientation marker on the ischium flange and/or pubic ramus flange of the implant.

In further preferred aspects of the invention the guide means of step b) and c) is in the form of a projection adapted to engage with the acetabular notch when the implant is correctly placed within the patient.

Preferably, the projection is an elongate projection extending outwardly from an upper region of the acetabular cup between the ischium flange and pubic ramus flange of the implant.

In further preferred embodiments, the method further includes the step of forming one or more suture holes in the implant.

More preferably, when the method includes manufacturing an acetabular implant, the method includes the step of forming one of more suture holes on the hemispherical acetabular cup of the implant.

Preferably, the additive manufacturing method is electron beam melting (EBM) manufacturing.

According to a seventh embodiment of the invention there is provided a method for the placement and orientation of an acetabular implant as described above within a patient, the method including the steps of;

a) placing the implant within a prepared patient acetabulum region;
b) aligning the at least one guide means on the implant with a reference point associated with patient bone.

According to an eighth embodiment of the invention there is provided a plugging system for use within a bone replacement implant, the plugging system including an aperture surround adapted to be connectably received within an aperture in a bone replacement implant; and a lid portion, wherein the lid portion and aperture surround are adapted to be releasably and/or lockingly connected to each other.

Preferably the implant and aperture surround are integrally formed.

Preferably, the lid portion and aperture surround are connectable using a threading mechanism, interference fit mechanism or lock and key mechanism.

Preferably the lid portion includes three dimensional scaffold on at least a portion of the lid portion surface.

Alternatively, at least a portion of the aperture surround and/or lid portion includes a rough surface finish with an Ra of between 1-25 μm.

In one embodiment of the invention the surface of the lid portion may be shaped to fit the contour of the implant in which the plugging system may be included. For example the upper surface of the lid portion may be concave, convex or curved to mimic the contours of the implant in which it is placed.

In further embodiments the lid portion of the plugging system may include a means for receiving a tool.

More preferably, the lid portion includes a means for receiving a screwdriver, hex key or other tool suitable for placement and removal of the lid portion.

In more preferred embodiments, the implant includes one or more suture holes.

More preferably, the implant is an acetabular implant and includes one or more suture holes located on the hemispherical cup of the implant.

More preferably, the implant includes between one and ten suture holes.

More preferably, the suture holes are circular or elliptical in shape.

Preferably, the one or more suture holes are located 5-40 mm from the edge of the hemispherical cup.

According to a ninth embodiment of the invention there is provided a closure means, the closure means adapted to cover an aperture and removably attach to the aperture edges in a bone replacement implant.

Preferably, at least one surface of the closure means includes three dimensional scaffold, or a roughened surface finish.

Preferably, the closure means includes a removal means to ensure the closure means can be removed from the implant if necessary.

In one further embodiment the surface of the closure means may be shaped to fit a specific bone implant in which the closure means may be placed. For example the surface of the lid portion may be concave, convex or curved to mimic the contours of the implant in which it is placed.

Preferably, the closure means is adapted to be removably attached to the implant using a threading mechanism, interference fit mechanism or lock and key mechanism.

According to an tenth embodiment of the invention there is provided a bone replacement implant, the implant including at least one aperture and a plugging system for said aperture as described above.

Preferably, the implant is an acetabular implant.

More preferably, the implant is an acetabular implant and the plugging system is located substantially in the base of the acetabular cup.

Even more preferably, the plugging system located in the base of the acetabular cup includes a concave lid portion to mimic the internal contours of the acetabular cup wall.

In more preferred embodiments, the implant includes one or more suture holes.

More preferably, the implant is an acetabular implant and includes one or more suture holes located on the hemispherical cup of the implant.

More preferably, the implant includes between one and ten suture holes.

More preferably, the suture holes are circular or elliptical in shape.

Preferably, the one or more suture holes are located 5-40 mm from the edge of the hemispherical cup.

According to a eleventh embodiment of the invention there is provided a method for the placement of bone graft behind a bone replacement implant that has been inserted and sealed within a patient, the method including the steps of;
a) selecting a bone replacement implant including an aperture and a plugging system as described above;
b) inserting implant into a patient, positioning and sealing the implant in known fashion, with or without the lid portion in position;
c) once the implant is in position and sealed, removing the lid portion of the plugging system within the implant if still in position;
d) packing bone graft through the aperture surround of the plugging system to an area or void behind implant;
e) replacing lid portion and locking into position to seal off aperture.

According to a twelfth embodiment of the invention, there is provided a bone replacement implant, wherein the implant includes at least two features selected from;
a) an area of three dimensional scaffold on two or more bone apposition surfaces associated with the implant;
b) an area of roughened surface texture located on substantially all outwardly facing surfaces of the implant not covered with a three dimensional scaffold structure;
c) at least one integrally formed guide means for facilitating correct alignment of the implant within a patient; and
d) an aperture and a plugging system, the plugging system including an aperture surround adapted for attachment to the aperture in the bone replacement implant; and a lid portion, wherein the lid portion and aperture surround are adapted to be releasably and/or lockingly connected to each other.

Preferably, the bone replacement implant is an acetabular implant.

Preferably, feature a) further includes features as described in more detail above in relation to the first embodiments of the invention.

Preferably, feature b) further includes features as described in more detail above in relation to the third embodiments of the invention.

Preferably, feature c) further includes features as described in more detail above in relation to the fifth embodiments of the invention.

Preferably, feature d) further includes features as described in more detail above in relation to the eighth and tenth embodiments of the invention.

In further embodiments there is provided a method of manufacturing the implant according to any one of the first, third, fifth, eight and tenth embodiments of the invention using additive manufacturing.

According to a thirteenth embodiment of the invention there is provided a method for the manufacture of a patient-specific bone replacement implant wherein the implant surface includes at least two features selected from;
- a) an area of three dimensional scaffold on two or more bone apposition surfaces associated with the implant;
- b) an area of roughened surface texture located on substantially all outwardly facing surfaces of the implant not covered with a three dimensional scaffold structure;
- c) integrally formed guide means for facilitating correct alignment of the implant within a patient; and
- d) an aperture adapted to receive a plugging system, the plugging system including an aperture surround adapted for attachment to the aperture in the bone replacement implant; and a lid portion, wherein the lid portion and aperture surround are adapted to be releasably and/or lockingly connected to each other;

wherein the method includes the steps of;
- e) extracting patient-specific information regarding a patient's specific bone geometry at said implantation site;
- f) designing a patient-specific implant based on said information in e) and further information relating to two or more of features a)-d);
- g) manufacturing implant based on the design of step (f) using additive manufacturing techniques.

Preferably, step f) further includes features as described in more detail above in relation to the second, fourth and sixth embodiments of the invention as discussed in further detail above.

Further aspects of the invention, which should be considered in all its novel aspects, will become apparent to those skilled in the art upon reading of the following description which provides at least one example of a practical application of the invention.

DESCRIPTION OF THE DRAWINGS

One or more embodiments of the invention will be described below by way of example only with reference to an acetabular implant or implant, and without intending to be limiting, with reference to the following drawings, in which.

DETAILED DESCRIPTION OF THE INVENTION

The implant, systems and methods of the present invention are described in further detail below and with reference to FIGS. 1-8.

The orthopaedic implants described in the current invention may be applied to a range of bone implants and implants, designed for use in any number of regions in the body and may also be applied to implants of varying shapes and sizes.

In a preferred aspect of the invention the implants and methods of the present invention are for use in acetabulum implants. However, this use is not intended to be limiting and as would be understood by a person skilled in the art, the methods, implant and systems described herein may include a range of implant designs and locations as necessary. The following description will for exemplary purposes be described in relation to an acetabular implant and associated methods.

Figure 4:
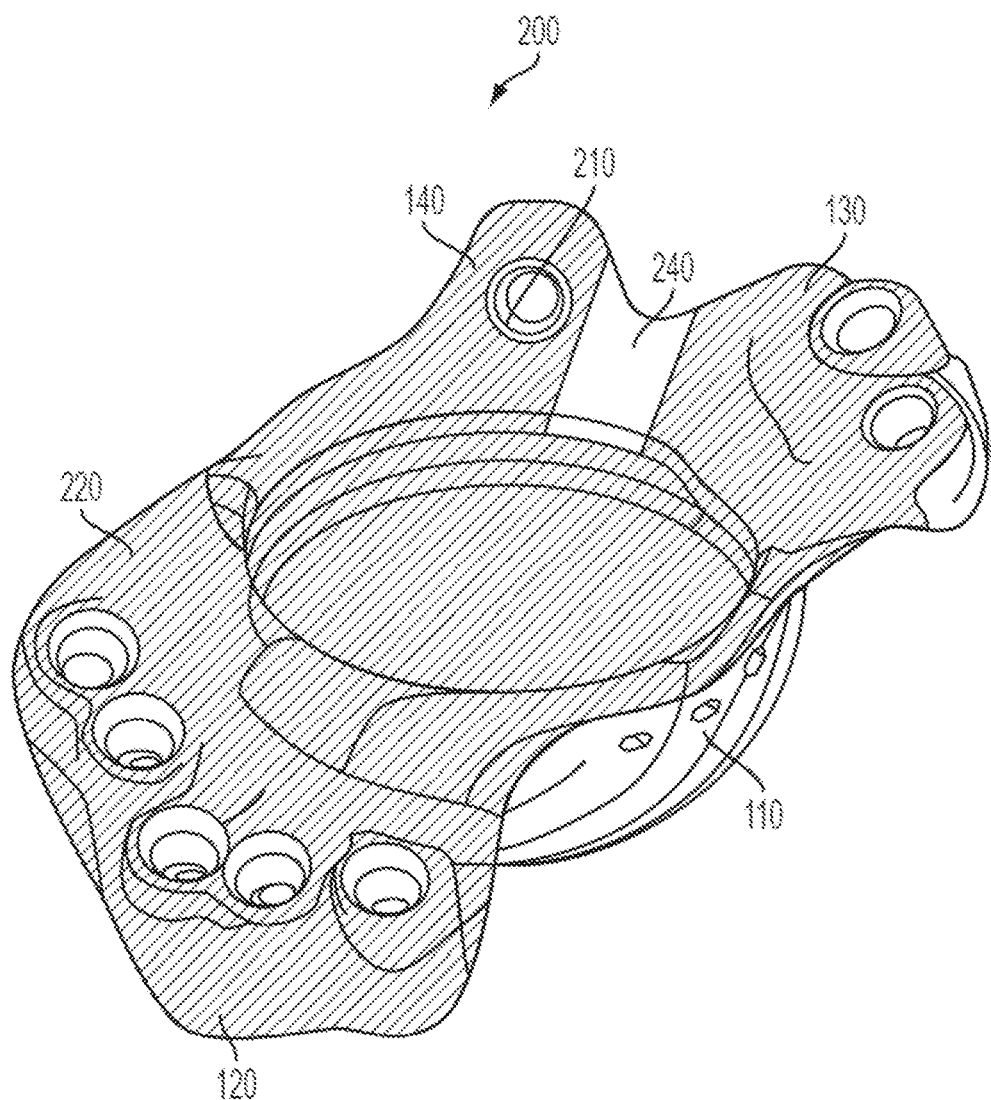
FIG. 4 shows a perspective view of an acetabular augment with a roughened surface in one preferred form of the invention.
Figure 5:
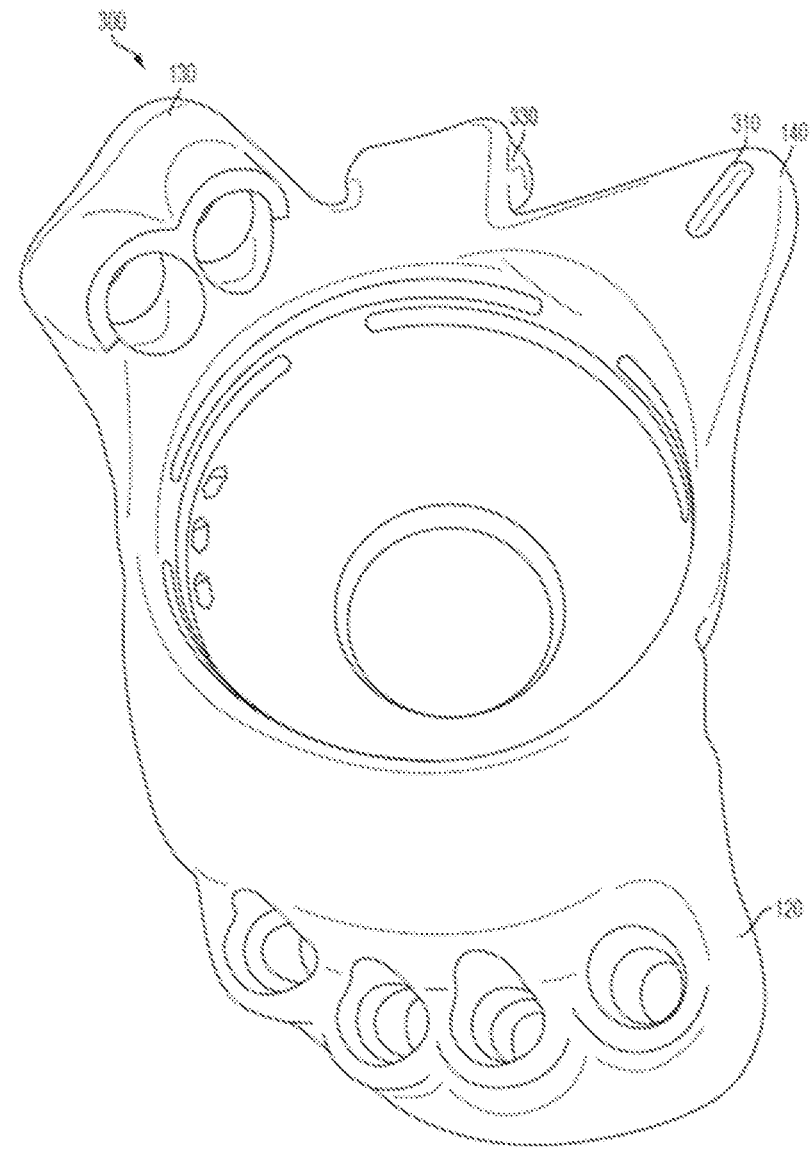
FIG. 5 shows a perspective view of an acetabular implant including orientation guides according to one preferred embodiment of the invention.

The figures include acetabular implants designed for both left and right hip replacements and therefore some figures will differ in orientation. For example the implant shown in FIG. 4 is designed for use with a patient's right hip, while FIG. 5 is designed for use with a patient's left hip, therefore the specific flanges are located in different places on each of these implant diagrams. The description below is intended to be applied to either the left or the right acetabular region.

Figure 1:
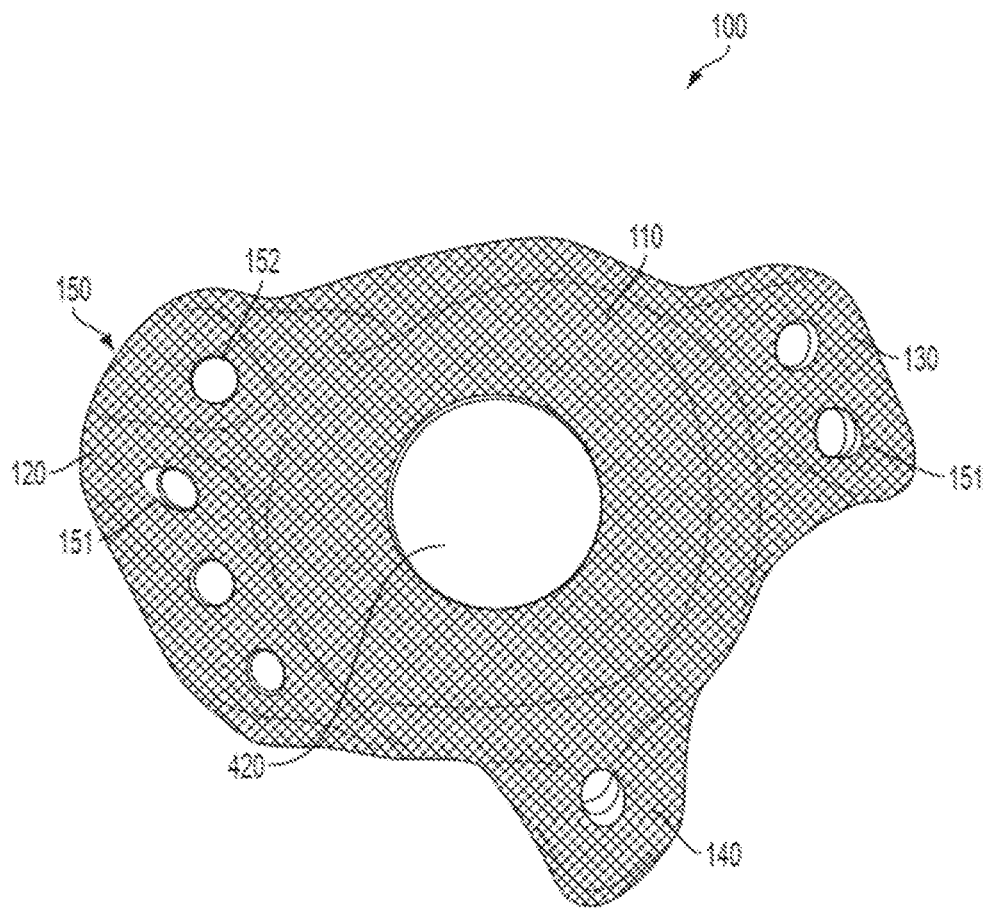
FIG. 1 shows perspective view of an acetabular implant with an integrally formed three dimensional scaffold region on all bone apposition surfaces according to one preferred embodiment of the invention.

A first aspect of the invention is shown with reference to FIG. 1 which shows a perspective view of an acetabular implant 100 with an integrally formed three dimensional scaffold region identified by crossed contour lines, the three dimensional scaffold located on regions of desired bone apposition.

Preferred acetabular implants of the present invention are patient-specific implants that include an acetabular cup portion 110 and three flanges extending from the rim of cup 110. These flanges are designed to enable fixation of the implant to the surrounding patient bone, and are typically classified as the ilium flange 120, ischium flange 130 and pubic ramus flange 140. When fixed to a patient, the flanges connect to the corresponding regions of patient anatomy, for example the ilium flange 120 contacts and is designed to correspond to and contour the ilium of the patient. Screw holes 152 are adapted for connecting implant 100 to bone.

In the preferred embodiments as shown in FIG. 1, which shows the underside of an acetabular implant, the three dimensional scaffold region is preferably positioned across all underside surfaces of the implant to enhance osseointegration of bone to the implant surface. This includes positioning of three dimensional scaffold underneath the acetabular cup 110 and on the bases and edges of any support flanges, in particular the ilium flange 120, pubic ramus flange 140 and ischium flange 130.

As seen in FIG. 1, the three dimensional scaffold forms a continuous surface over the underside of the acetabular cup 110 and flanges 120, 130 and 140 with no breaks or regions of polished metal surface. This continuous surface allows for maximum osseointegration of bone with the implant surface. In some preferred embodiments, the scaffold region extends over the lip 150 of the flanges to further improve osseointegration at this region.

When applied to an acetabular implant, the three dimensional scaffold on the under surface and the edges of the flanges 120, 130 and 140 allows osseointegration and encourages the periosteal new bone to grow up over the flange. This results in improved long term fixation from bone growth over the flanges and rim loading, as well as from the underside of the acetabular cup 110.

Figure 2:
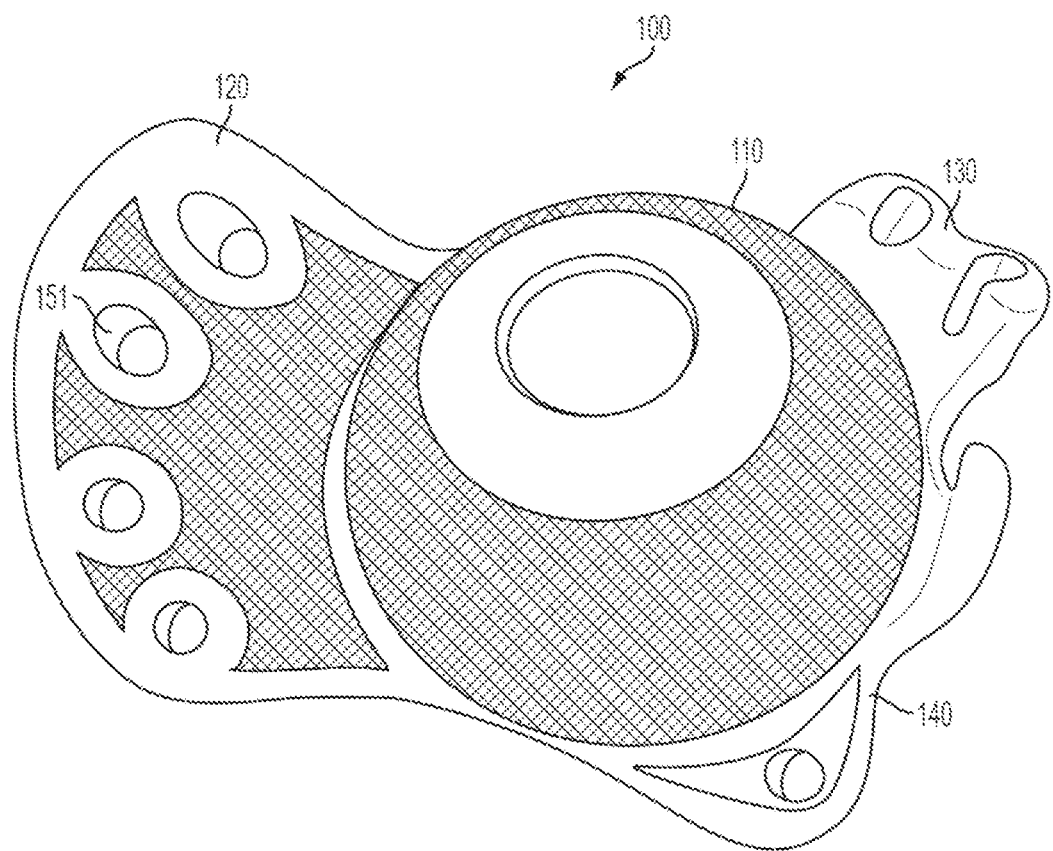
FIG. 2 shows an acetabular implant with three dimensional scaffold located on the undersides of the acetabular cup and the ilium flange in one preferred form of the invention.

FIG. 2 shows an acetabular implant in a further embodiment where mesh shown by cross hatched lines is located on the underside of the acetabular cup 110 and the underside of the ilium flange 120, but does not reach the edges of the implant 100. This mesh positioning is adapted to suit the requirements of individual patients and mesh may be located in areas of maximum bone apposition. In some circumstances, flanges may not be large enough to accommodate mesh once a screw hole has been positioned on the flange and mesh may or may not reach the edges of the flange at different locations on the implant surface. In such situations mesh may be located on one or two flanges only for example, as seen in FIG. 2.

Preferred three dimensional scaffold of the present invention is integrally formed during the formation of an acetabular implant using additive manufacturing technologies, in particular EBM manufacturing which achieves a preferred surface finish on manufactured implants.

The preferred three dimensional scaffold structure for use in the present invention is a three dimensional modified dodecahedron structure with an individual unit cell structure of between 1.0 mm and 3.0 mm. Maintaining unit cell size is important to increase the chances of effective osseointegration with the implant. If unit cell size is too small, the three dimensional scaffold becomes difficult to clean and sterilise prior to use. If the unit cell size becomes too large, the structure loses mechanical integrity and osseointegration may also not be achieved as readily with a more spacious three dimensional scaffold structure.

As would be clear to a person skilled in the art, the style of three dimensional scaffold structure discussed above is not intended to be limiting and it is envisaged that other formations of three dimensional scaffold that are mechanically sound may be used in the method and products of the present invention.

Other formations of three dimensional scaffold may include a range of different shaped scaffold members that are connected to form a structural sound lattice, often formed from "unit cells". A unit cell for the purposes of describing the scaffold structure may be a void defined by scaffold members on all sides. For a dodecahedron structure, the unit cell would be the three dimensional area inside the dodecahedron. Other unit cell shapes may be substantially spherical, oval, cube, cuboid, cylindrical, hexagonal, octagonal or triangular prisms for example. Alternatively the unit cell may have an irregular three dimensional shape wherein the unit cells throughout the scaffold are not uniform but formed by an arrangement of plate and rod like structures that create a lattice similar to that found in trabecular bone tissue within human bone.

Screw threads 151 are not intended to include three dimensional scaffold as would be clear to a person skilled in the art.

Figure 3:
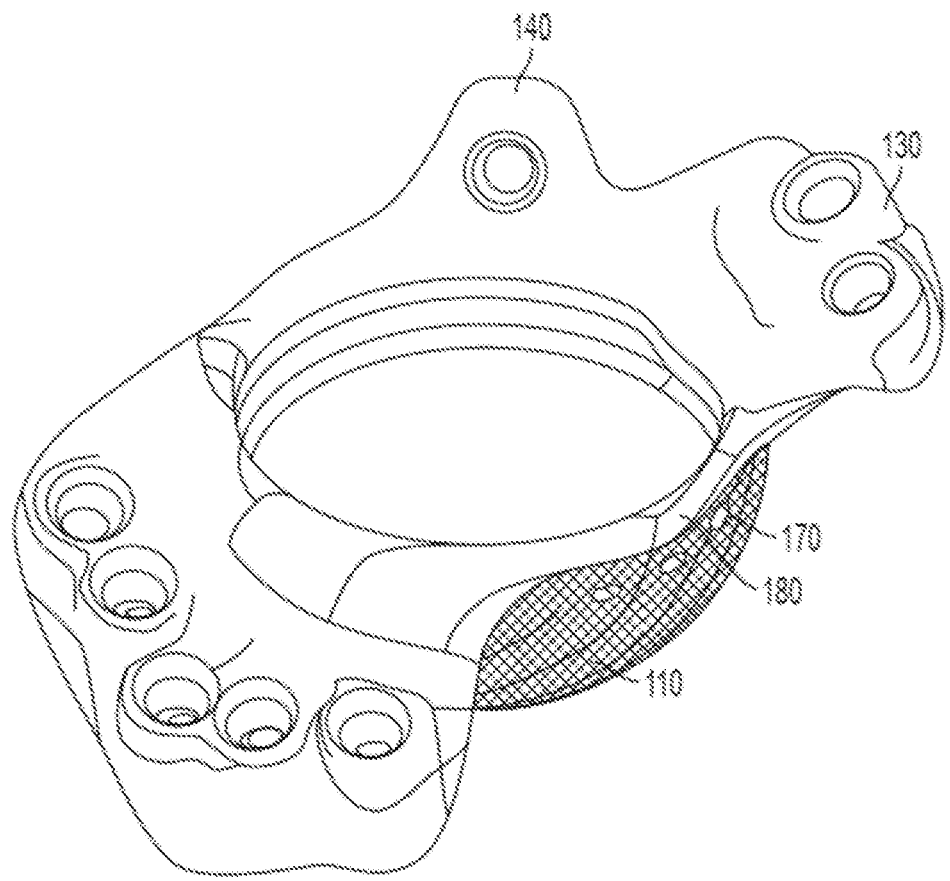
FIG. 3 shows an upper perspective view of an acetabular augment in one embodiment of the invention including suture holes in the acetabular cup.

FIG. 3 shows an acetabular implant of the present invention wherein mesh is located on the underside of hemispherical acetabular cup 110 and underneath the flanges (mesh not seen in FIG. 3). Also present on the side wall of acetabular cup 110 are suture holes 170. Suture holes 170 are preferably integrally formed within the wall of acetabular cup 110 and are designed to enable the articular capsule to be sutured on to the implant.

Such suture holes may be any shape but are preferably circular, oval or elliptical and are approximately 2-6 mm in diameter or width and are located 5-40 mm from rim 180 of the acetabular cup. The number of suture holes will depend on the size and shape of the implant, with more or less suture holes incorporated as required. In typical implants between two and six suture holes are likely to be required, however more or less may be added as needed.

Suture holes 170 may be incorporated at other locations on the implant to further enable attachment of the implant to bone. Such locations may include other regions of the acetabular cup, or on flanges to enable the implant to be further secured to soft tissue or bone once fixed in position.

FIG. 4 shows a further embodiment of the invention in relation to an acetabular implant 200 wherein the implant 200 includes a roughened textured surface (indicated by diagonal lines) on the areas of an implant (for example 220) where three dimensional scaffold structure is not required. Three dimensional scaffold structure is typically placed on the underside of the implant where osseointegration will occur.

As with the acetabular implant shown in FIGS. 1-3, the preferred acetabular implants incorporating a roughened surface texture are patient-specific implants that include an acetabular cup portion 110 and three flanges 120, 130 and 140 extending from the rim of cup 110.

Preferably, the roughened textured surface is located on substantially all surfaces that are outward facing once the implant has been correctly positioned within a patient, so as to enhance integration of the implant with the soft tissues of the recipient acetabulum and surrounding areas. As would be clear to a person skilled in the art, surfaces of the implant such as screw threads 210 for example will not include a roughened surface as smooth surfaces are required for effective attachment of screws or other attachment means.

Roughened surfaces may be produced using the additive manufacturing, preferably EBM manufacturing to the exact required surface roughness, or alternatively surfaces may be sanded or altered post-manufacturing to achieve the exact surface required. Preferably the roughened surface has an Ra value of between 1-20 μm, with the higher Ra values indicating a rougher surface.

The inventors have found that high Ra values are more effective in producing effective osseointegration of bone with an implant, however this is not intended to be limiting.

When used in an acetabular implant, the surface adjacent to the gluteal muscles and around the rest of the implant includes a roughened textured surface so that the soft tissues adhere. This stops the formation of a fluid filled sack through which pressure can be transmitted to cause flow and "waterchisel" out the interfaces. It also significantly increases the dead space in which bacteria can grow/contaminate and form an abscess.

It should be appreciated that small regions of polished, smooth surface may be included in the implant where rough surface may cause tissue damage. As shown in FIG. 4, a portion of the acetabular rim 240 located between pubic ramus flange 140 and ischium flange 130 may be polished in order for soft tissue to pass over the rim without being damaged by a roughened surface. This region in particular is where the psoas tendon may run if the fibrous capsule has been removed or is absent. In patient-specific implant design exact placement of such polished areas may be defined and manufactured based on individual information regarding patient anatomy. Other areas of implants of the present invention may include polished, smooth regions where the implant makes specific contact with fragile or moveable soft tissue, such as nerves, blood vessels, tendons, ligaments etc.

The roughened textured surface and the three dimensional scaffold covered surfaces indicated by FIGS. 1-4 are preferably coated with a bacterial resisting surface to prevent or deter possible infection. One such coating that may be used is an ion beam silver sputter coating. As would be appreciated by a person skilled in the art, a range of different known anti-bacterial coatings may be applied to the surfaces in order to reduce infection risk during and post-surgery.

Figure 6:
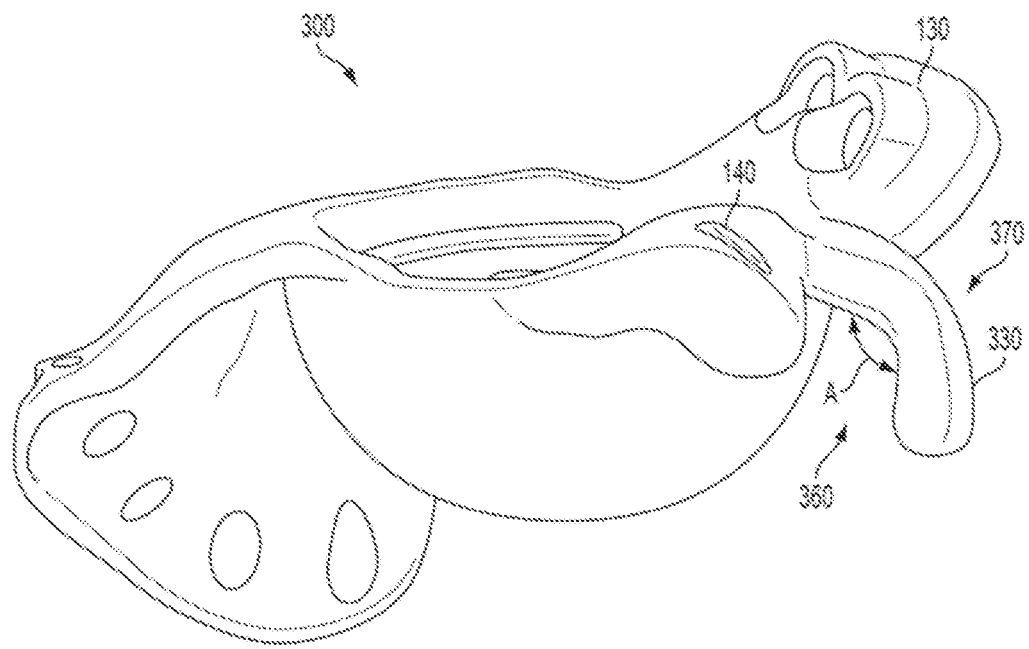
FIG. 6 shows a side perspective of the implant shown in FIG. 5.

In a further embodiment of the invention the bone replacement implant may include one or more orientation guides as shown in FIGS. 5 and 6. Correct orientation of an implant within a patient is vital to enable successful placement of the attachment mechanisms (e.g. screws) as well as ensuring a successful fit within the patient itself.

Placement of implants within a patient can often be difficult, as alignment must be correct in a range of directions, and typically space is restricted due to the limits of the surgical opening in the patient.

As shown in FIG. 5, where a tri-flange acetabular implant 300 is exemplified, a first orientation guide 310 is positioned on the pubic ramus flange 140 in the form of a linear groove so as to substantially align with the patient's pubic ramus ridge when the implant 300 is inserted in the correct position within a patient. This orientation line is typically a linear line running substantially perpendicular to the acetabular rim along the pubic ramus flange, from a first point proximate the acetabular rim to a second point proximal to the outer edge of the pubic ramus flange. This alignment between pubic ramus ridge and orientation marker on the implant enables exact correct placement of an attachment means locating through the pubic ramus flange 140 of implant 300 which is crucial in an acetabular implantation. In other examples not shown, the orientation guide or groove may be positioned on the ischium flange 130, or at other positions within the implant to enable correct alignment of the implant 300.

Such an orientation guide 310 is particularly useful on the pubic ramus as the bone is relatively narrow.

In preferred embodiments the alignment means is in the form of a linear depression showing a central guide line down the length of the depression. The linear depression is recessed into the pubic ramus flange, allowing the specialist to feel the alignment direction tactilely as well as see it visually. If space is limited when positioning the implant, having a recessed alignment means allows the specialist to align the implant correctly using touch. In other embodiments the alignment means may be raised from the implant surface to form a guide means the can be read visually as well as tactilely.

A raised or depressed orientation guide 310 may be incorporated at various other locations on an implant as required by patient-specific needs.

In further preferred aspects of the invention when applied to an acetabular implant, the implant may further include a guide means in the form of a projection 330 adapted to engage with a patient's acetabular notch when the implant 300 is correctly placed within the patient.

In one preferred embodiment, projection 330 is located between the ischium 130 and pubic ramus 140 flanges of the implant 300 shown in FIGS. 5 and 6. Projection 330 is in the form of an elongate flange and extends away from the upper ridge of the external surface of the hemispherical cup of the acetabular implant. Projection 330 preferably includes a bend, corner or curve of at least substantially 90° or more as shown by angle A in FIG. 6. This curve A enables projection 330 to fit around the acetabular notch of a patient, securing the implant in position. The exact angle will be dependent on the specific bone geometry of the individual patient, however as would be understood by a skilled person, a projection with a very acute angle less than 90° would be difficult to position, as tight angles would need to be negotiated to position the implant in place.

Projection 330 may be of varying widths and lengths as dictated by the patient-specific data, however limitations are introduced by the size and position of the ischium and pubic ramus flanges.

Projection 330 may also include an area of three dimensional scaffold or roughened surface texture on any of the projection surfaces to aid in osseointegration with bone and adherence to surrounding soft tissue. In one embodiment projection 330 is formed from Ti6Al4V and includes an area of three dimensional scaffold on at least the under surface of the projection indicated by arrow 360 on FIG. 6 and includes an area of roughened surface texture on the upper surface of the projection indicated by arrow 370.

It is envisaged the other projections may be used in a range of implants where additional guide means extending from the implant may improve correct seating of implants within a patient.

Figure 7:
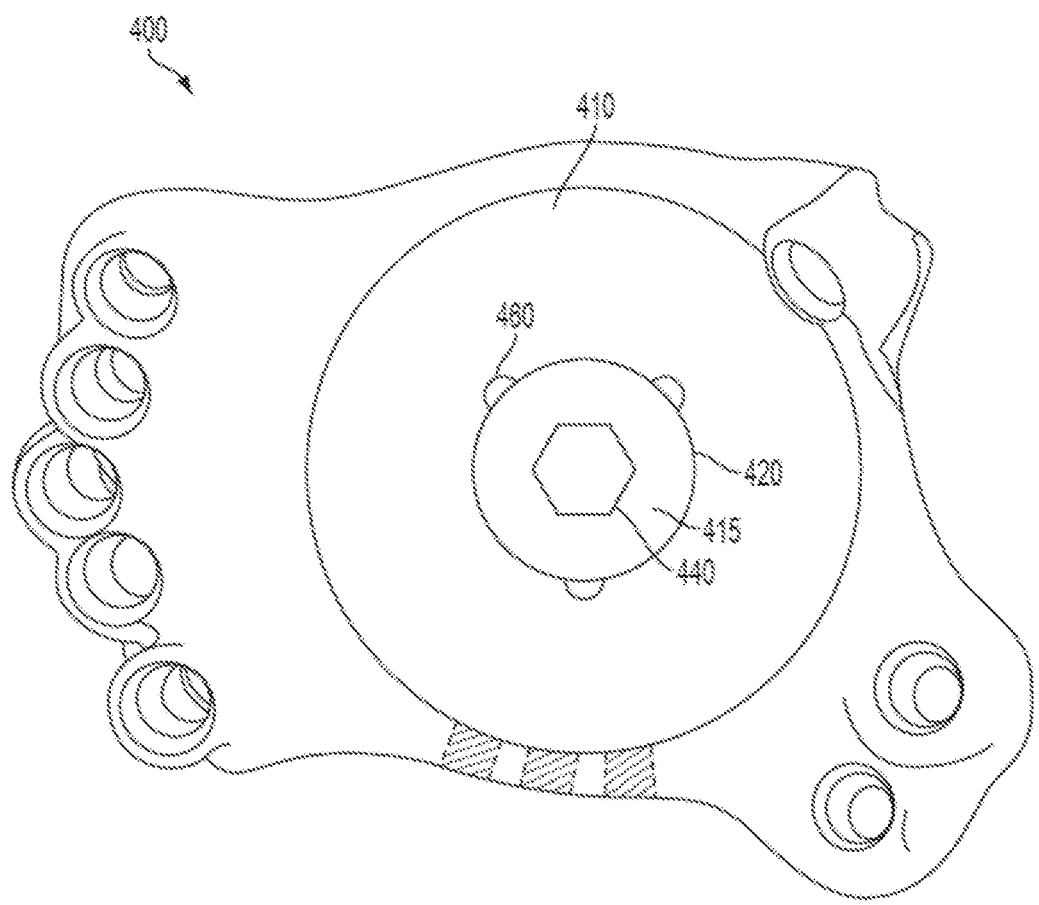
FIG. 7 shows a perspective view of an acetabular implant including an aperture and plugging system according to one preferred embodiment of the invention.
Figure 8:
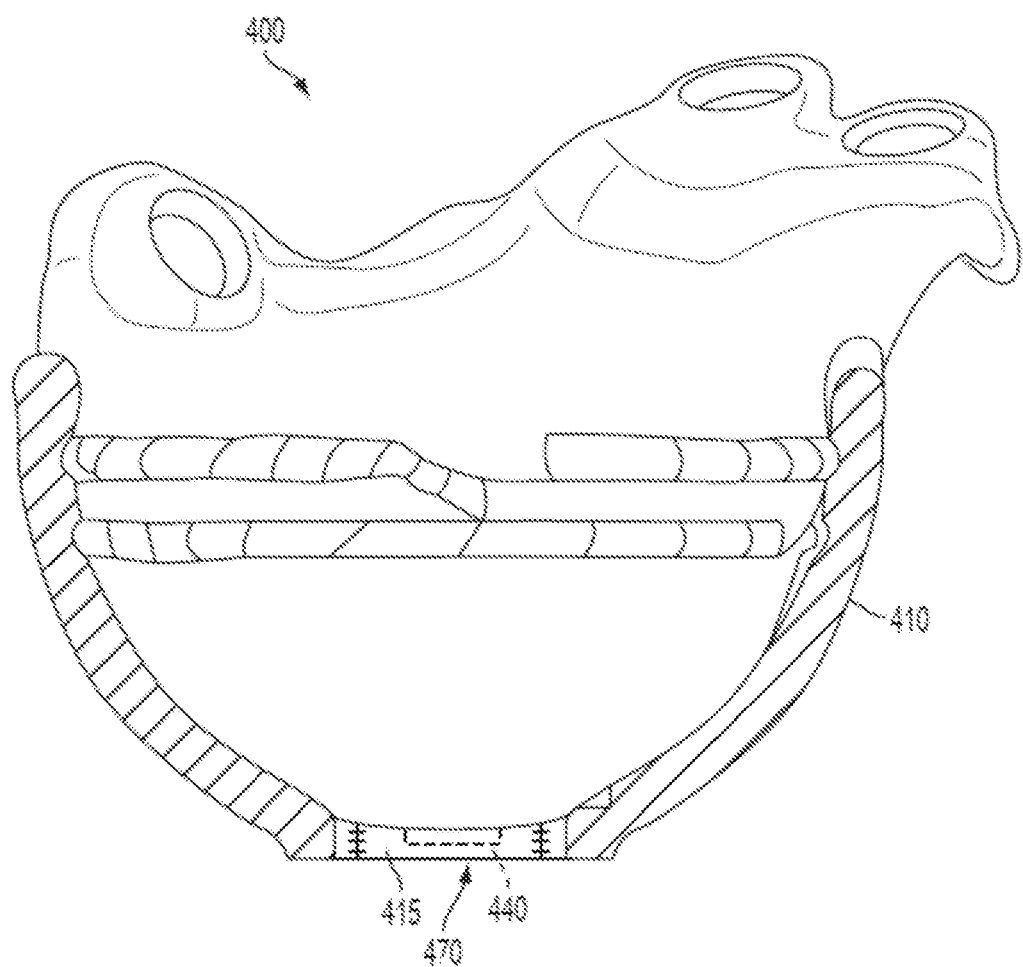
FIG. 8 shows a side cross section of the implant as shown in FIG. 7 in one preferred embodiment of the invention.

FIGS. 7 and 8 show one embodiment of the invention wherein an acetabular implant 400 is formed with an aperture 420 (also seen clearly in FIG. 1) located at the base of the acetabular cup 410, and includes a plugging system 430 to enable placement of bone graft behind implant 400 once implant 400 has been positioned and seated within a patient.

The plugging system of the present invention includes an aperture surround (not shown) adapted for attachment to an aperture 420 in a bone replacement acetabular implant 400 and a lid portion 415, wherein the lid portion 415 and aperture surround are adapted to be releasably and/or lockingly connected to each other.

The presence of the aperture 420 within the implant 400 and the plugging system 430 provides the ability to access behind the implant 400 to restore bone stock and provide further stability by introducing grafted bone to any dead space located behind the implant once seated. Without the aperture 420 and plugging system 430 of the present invention, bone graft must be packed into any dead space prior to seating of the bone graft. This introduces difficulties in seating the implant, as the bone graft surface may not be smooth, or alternatively, may not fill the dead space entirely.

The plugging system 430 enables bone graft to be packed behind the implant, then enables complete sealing of the aperture to ensure the integrity of the implant is not compromised. In preferred plugging system design, the system includes an aperture surround which is integrally formed within the aperture, for example in the form of an aperture with threaded interior walls.

Other connection means may be located either integrally formed with the aperture or as part of a separate aperture surround. For example, connections means such as lock and key mechanisms, interference or friction fit mechanisms may be used to create a tight seal between the aperture and the lid portion of the plugging system.

Alternatively the aperture surround may be formed separately then retrofitted to an aperture in an implant using known attachment techniques.

The plugging system also includes a lid portion 415. Lid portion 415 complements the aperture surround in order to create a releasably locking connection means. Lid portion 415 is preferably designed such that when in the closed position, lid portion 415 is shaped to fit the contour of the implant in which it is placed. For example, when positioned in the base of an acetabular cup, lid portion 415 may include a concave upper surface (not shown). This allows the geometry of the implant to be unaffected by the plug, allowing for example bone cement to be placed over the lid portion at a usual thickness.

Lid portions or closure mechanisms of the present invention may also include means for inserting or removing the lid portion or closure means from within an aperture in an implant, for example the hex key depression 440 shown in FIGS. 7 and 8. In use, the lid may be threaded into position within an aperture surround then tightened or loosened using a hex key which fits into depression 440. Other suitable means not indicated in the Figures include means to receive a screwdriver, hook, handle or other fastening or loosening means as would be appreciated by a person skilled in the art. It should be appreciated that any such feature is preferably a negative feature to ensure that any corresponding femoral head is able to smoothly rotate within the acetabular cup region without being damaged.

When a press fit mechanism is used to secure a lid portion 415 to the aperture surround, removal means 460 may be included in the inner base of the acetabular cup. These removal means allow the user to insert a tool to remove the lid portion if necessary.

In one preferred embodiment of the invention, an acetabular implant includes an aperture in the base of the acetabular cup, the edges of the aperture including a threaded wall adapted to receive a corresponding threaded lid portion adapted to fit and be received into the aperture in the base of the acetabular cup. One in position, the lid can be tightened or loosened by use of a hex-key that can be received into a hexagonal shaped depression in the lid surface.

It is preferable that the base of the lid portion 470 includes a similar surface to the base of the acetabular cup portion of the implant. This will preferably be, but is not limited to a three dimensional mesh or scaffold. The presence of a three dimensional scaffold on the underside of the lid portion aids in osseointegration of the bone graft packed behind the lid with the implant, increasing the strength of the bond between the patient and implant.

The manufacturing methods of the present invention may include the use of patient-specific information to create an implant that specifically matches the bone morphology of the patient at the insertion location. This information allows for design and positioning of features of the present invention, such as three dimensional scaffold, roughened textured surfaces, orientation guides and/or apertures and plugging systems.

Patient-specific information regarding structural anatomy can be collected by a variety of known means, such as CT scanning, X-rays, MRI scans or radiography techniques for example.

In manufacturing the implants of the present invention, such patient-specific information is gathered and a model of a patient-specific implant is developed based on the inclusion of features of the present invention that are likely to result in the most successful replacement outcome for the patient.

The model is then used to manufacture the patient-specific implant using additive manufacturing techniques, preferably EBM manufacturing. Following manufacture of the implant, the implant is then surface finished if necessary and any further features added such as screw placement holes or additional orientation markers for example. The implant is then cleaned and sterilised before being provided to a hospital or surgical professional for use.

While the preferred additive manufacturing technique is EBM manufacturing, other techniques such as selective laser melting (SLM) may also be used. The implants of the present invention are preferably made from Ti6AL4V, however other metals that may be used include alternative titanium alloys, tantalum, stainless steel or cobalt-chromium or alloys thereof.

The apparatus and methods described in the current application have a number of advantages over implants and methods for their manufacture currently known in the art.

Implants of the present invention may include one or more of the embodiments outlined in this description, as required by specific needs of individual patients.

In a preferred embodiment, the implant of the invention is a patient-specific tri-flange acetabular implant, with ilium, ischium and pubic ramus flanges incorporating two or more of the features described above. In some embodiments, the implant will include all of the features. This exemplary implant includes an integrally formed three dimensional scaffold on the underside of the acetabular cup and the underside of at least two of the three flanges to aid in osseointegration at all bone-implant interfaces. In circumstances where flanges are large enough to incorporate scaffolding in addition to apertures for screw connections, the scaffold may be located on the underside of all three flanges where they will connect to patient bone when in position.

The upper surfaces of each of the flanges and the internal surface and rim of the acetabular cup include a roughened surface finish. Typically, such surfaces are polished smoothly, however by incorporating a textured finish to these surfaces integration with surrounding soft tissue is enhanced. One area of the acetabular implant that has a polished, smooth surface is the often the medial wall of the acetabular rim, between the pubic ramus and ischium flanges. This smooth surface allows the psoas tendon to run over the rim, with any risk of abrasion or damage from moving across a roughened surface.

The implant further includes an orientation line along the upper roughened surface of the pubic ramus flange, to aid in aligning the implant during implantation. This orientation line is typically a linear line running substantially perpendicular to the acetabular rim along the pubic ramus flange, from a first point proximate the acetabular rim to a second point proximal to the outer edge of the pubic ramus flange. The implant further includes an elongate projection extending from the acetabular rim between the pubic ramus flange and the ischium flange, the projection adapted to connect to the acetabular notch when the implant is positioned within a patient.

The implant further includes and aperture in the base of the acetabular cup, the aperture adapted to receive a closure mechanism that may be fitted in position within the base of the cup after the implant has been positioned within a patient.

The positioning of three dimensional scaffold over substantially all the bone apposition surfaces of an implant increases the potential for osseointegration of the bone to the implant when compared to levels of osseointegration of bone with the implant across polished or smooth surfaces. Extending the three dimensional scaffold region to cover edges and corners of some of the implant surfaces further encourages new bone growth around the implant, increasing stabilisation of the implant within the patient over time and therefore improving chances for a successful replacement result.

Likewise, the use of roughened, textured surfaces on implant surfaces not incorporating three dimensional scaffold for improves the adherence of soft tissue to the implant. Known implants and implants often have a large surface area that are formed from polished or smooth surfaces, which is less effective in facilitating regeneration of soft tissue around the implant than the use of roughened, textured surfaces.

The inclusion of orientation guides integrally formed within an implant improves the accuracy of seating an implant in the correct position within a patient site. Orientation guides that are integrally formed when manufacturing patient-specific implants are positioned exactly to achieve the optimum placement of each individual patient. The more accurate the seating of the implant is, the more successful the replacement procedure will be.

Effective packing of bone graft underneath or behind an implant in a patient is typically a difficult process, as dead space areas are often difficult to access or to pack effectively and still allow optimal seating of an implant on top of the packed bone graft. The inclusion of the plugging systems of the present allow for access to the underside or rear of the implant after it has been seated within a patient, allowing bone graft to be packed to an exact level without influencing the seating of the implant and also allowing access to areas that may previously not have been reachable. The ability to seal and lock the plug to recreates the implant surface, allowing it is function as if there were no aperture in place.

As with the above improvements, this increases the chances of the implant being successfully incorporated within the patient.

The suture holes discussed for incorporation into the implants of the current invention provide additional strength and support when locating the implant within a patient. In particular, suture holes in the acetabular cup allow for the acetabular capsule to be connected directly back on to the implant. Such suture holes may be incorporated at any position on the implants as necessitated by the patient's specific requirements.

The manufacturing methods described herein to produce implants with the above inventive features allow formation patient-specific implants that have a range of improved features integrally formed within the implant. This not only reduces labour costs, but allows for the creation of robust, effective and often single piece implants that result in large improvements in patient outcomes.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

We claim:

1. A single-piece acetabular implant formed using additive manufacturing, the acetabular implant including a hemispherical cup portion and an acetabular rim surrounding the perimeter of the hemispherical cup, and an ischium flange, a pubic ramus flange and an ilium flange, each flange extending outwardly from the perimeter of the hemispherical cup portion or acetabular rim;

wherein the ischium flange, ilium flange and pubic ramus flange each include a first upper surface extending continuously from the hemispherical cup or acetabular rim and a second opposing lower surface adapted to contact or partially contact bone when the implant is correctly seated within a patient; and wherein an implant surface further includes an area of integrally formed, porous three dimensional, open mesh scaffold having a pore unit cell size of between 1.0 mm and 3.0 mm, on the second lower surface of every flange and on a bone apposition surface of the hemispherical cup portion of the implant.

2. The implant as claimed in claim 1, wherein the porous, three dimensional mesh scaffold is formed over the edge(s) of one or more flanges from the second lower surface to cover an area of the first upper surface of the one or more flanges or over an area of the implant between the first upper surface and the second lower surface.

3. The implant as claimed in claim 1, wherein the porous, three dimensional mesh scaffold has a porosity of between 50% and 80%.

4. The implant as claimed in claim 1, wherein the implant includes one or more suture holes.

5. The implant as claimed in claim 1, wherein the implant is a patient specific acetabular implant.

6. The implant as claimed in claim 1, wherein the implant further includes one or more areas of non-porous, rough, textured surface on the first upper surface of one or more flanges.

7. The implant as claimed in claim 6, wherein the hemispheric cup portion has a concave inner surface covered by the non-porous, rough, textured surface.

8. The implant as claimed in claim 7, wherein the acetabular rim includes one or more regions of smooth surface and one or more regions of the non-porous, rough, textured surface.

9. The implant of claim 8, wherein the acetabular rim has a non-porous, rough, textured surface around substantially the entire circumference of the acetabular rim, excluding a region of the acetabular rim between the ischium and pubic ramus flanges, which includes a region of smooth surface.

10. The implant of claim 9, wherein the pubic ramus flange and ischium flanges are connected by a central flange portion extending outward from the acetabular rim, wherein the central flange portion includes a region of smooth surface.

11. The implant of claim 10, wherein the region of smooth surface is between 5 mm-25 mm in length extending substantially perpendicular to the acetabular rim and covers a region including a portion of the concave wall of the hemispherical cup, a portion of the acetabular rim of the implant and a portion of the central flange.

12. A method for the manufacture of a patient-specific acetabular implant, the method including the steps of;

a) extracting patient-specific information regarding a patient's specific bone geometry at said implantation site;

b) designing a patient-specific implant based on said information, the implant design including a hemispherical cup portion and an acetabular rim surrounding the perimeter of the hemispherical cup, and an ischium flange, a pubic ramus flange and an ilium flange, each flange extending outwardly from the hemispherical cup portion; wherein the ischium flange, ilium flange and/or pubic ramus flange each include a first upper surface extending continuously from the acetabular rim of the hemispherical cup and a second opposing lower surface adapted to contact or partially contact bone when the implant is correctly seated within a patient; and wherein the implant further includes an area of integrally formed, porous three dimensional open mesh scaffold having a unit cell size of between 1.0 mm and 3.0 mm, on a bone apposition surfaces of the hemispherical cup portion and on the second lower surface of every flange;

c) manufacturing the implant based on design of step (b) using additive manufacturing techniques, the manufacturing including the step of integrally forming the porous, three dimensional mesh scaffold with the implant.

13. The method of claim 12, wherein the method includes the step of forming the porous, three dimensional mesh scaffold over the edge(s) of one or more flanges from the second lower surface to cover an area of the first upper surface of the one or more flanges or over an area of the implant between the first upper surface and second lower surface.

14. The method of claim 12, wherein method includes the steps of forming one or more areas of non-porous, rough, textured surface on the first upper surface of one or more flanges.

15. The method of claim 14, wherein the method includes the step of forming the acetabular rim with one or more regions of smooth surface and one or more regions of the non-porous, rough, textured surface.

16. The method of claim 15, wherein the method includes the step of forming the acetabular rim with a non-porous, rough, textured surface around substantially the entire circumference of the acetabular rim, excluding a region of the acetabular rim between the ischium and pubic ramus flanges, which includes a region of smooth surface.

17. The method of claim 12, wherein the method includes the step of forming pubic ramus flange and ischium flanges connected by a central flange portion extending outward from the acetabular rim, wherein the central flange portion includes a region of smooth surface.

* * * * *